US008517971B2

(12) United States Patent
Creedon et al.

(10) Patent No.: US 8,517,971 B2
(45) Date of Patent: Aug. 27, 2013

(54) CANNULA IMPLANT DEVICE FOR USE IN SALIVARY GLAND DUCTS

(75) Inventors: Dennis Creedon, Sandwich, MA (US); Lewis H. Marten, Westwood, MA (US); Barry Michael Schaitkin, Pittsburgh, PA (US)

(73) Assignee: E. Benson Hood Laboratories, Pembroke, MA (US)

( * ) Notice: Subject to any disclaimer, the term of this patent is extended or adjusted under 35 U.S.C. 154(b) by 127 days.

(21) Appl. No.: 13/180,187

(22) Filed: Jul. 11, 2011

(65) Prior Publication Data

US 2012/0010555 A1    Jan. 12, 2012

Related U.S. Application Data

(60) Provisional application No. 61/362,985, filed on Jul. 9, 2010, provisional application No. 61/423,968, filed on Dec. 16, 2010.

(51) Int. Cl.
*A61M 1/00* (2006.01)

(52) U.S. Cl.
USPC ........... 604/8; 604/6.16; 606/153; 623/23.64; 623/23.7

(58) Field of Classification Search
USPC ... 604/8, 6.16, 264; 606/153; 623/23.6–23.7
See application file for complete search history.

(56) References Cited

U.S. PATENT DOCUMENTS

| 6,110,185 A * | 8/2000 | Barra et al. ............... 606/148 |
| 2007/0162148 A1 * | 7/2007 | Nahlieli ....................... 623/23.7 |

OTHER PUBLICATIONS

Tim Buckenham. Salivary Duct Intervention. Seminars in Interventional Radiology/vol. 21, No. 3, 2004, pp. 143-148.*
Aslam et al.. Technical Report: Wire Guided Sialography. Clinical Radiology. vol. 44, Issue 5, 1991. p. 350-351.*

* cited by examiner

*Primary Examiner* — Loan Thanh
*Assistant Examiner* — Andrew S Lo
(74) *Attorney, Agent, or Firm* — Frommer Lawrence & Haug LLP; Ronald R Santucci

(57) ABSTRACT

A cannula for placement within a salivary gland duct having a first end adjacent an oral cavity and a second end adjacent a salivary gland is provided. The cannula includes an elongate body having a lumen and a first and a second plate offset from a proximal end of the elongate body. The first plate is located on one side of the elongate body and the second plate is correspondingly located on the other side of the elongate body and adjacent the first plate. The first plate has a first hole that is operable to suture the first plate to a location adjacent the first end of the salivary duct adjacent the oral cavity, whereby upon placement of the cannula within the salivary gland duct, saliva flows through the elongate body's lumen from the salivary gland to the oral cavity.

1 Claim, 9 Drawing Sheets

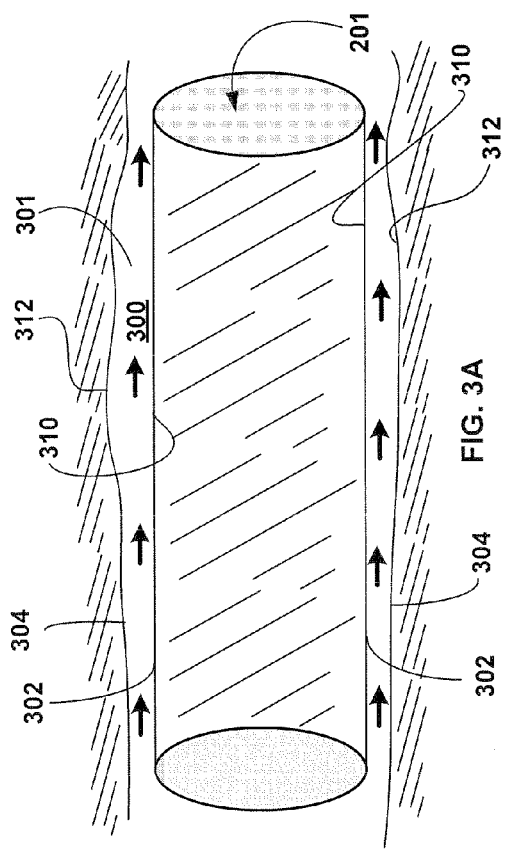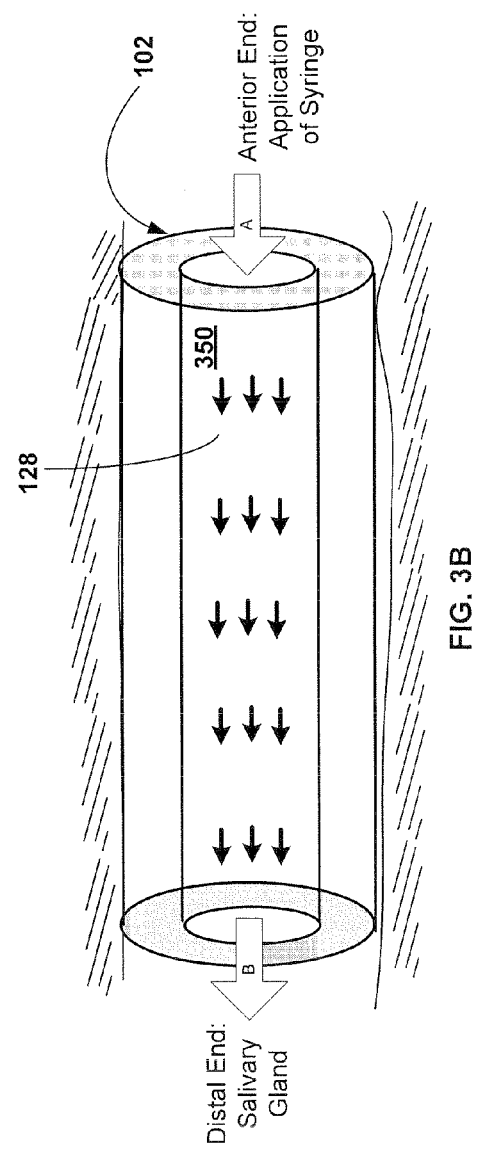

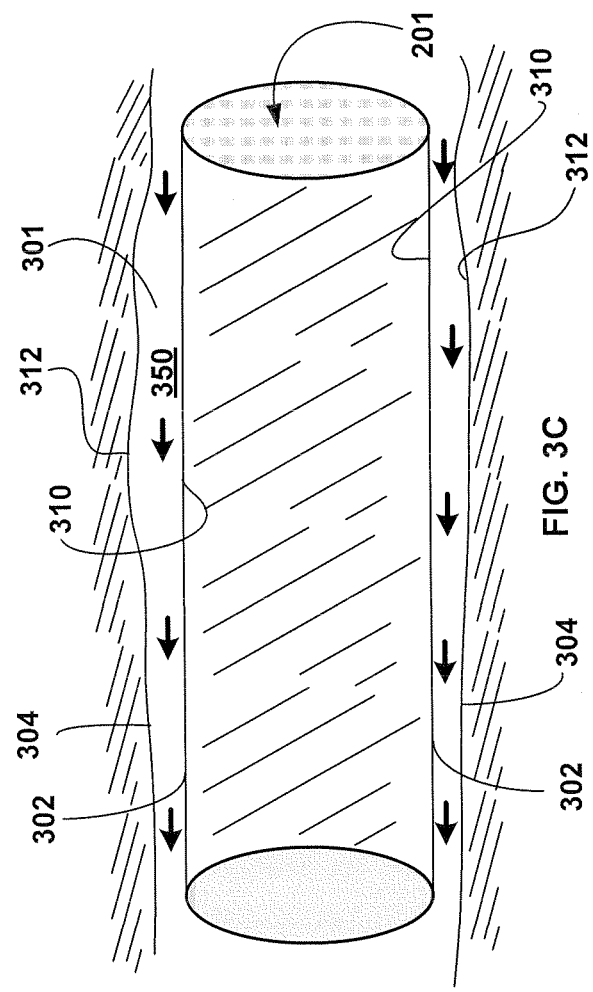

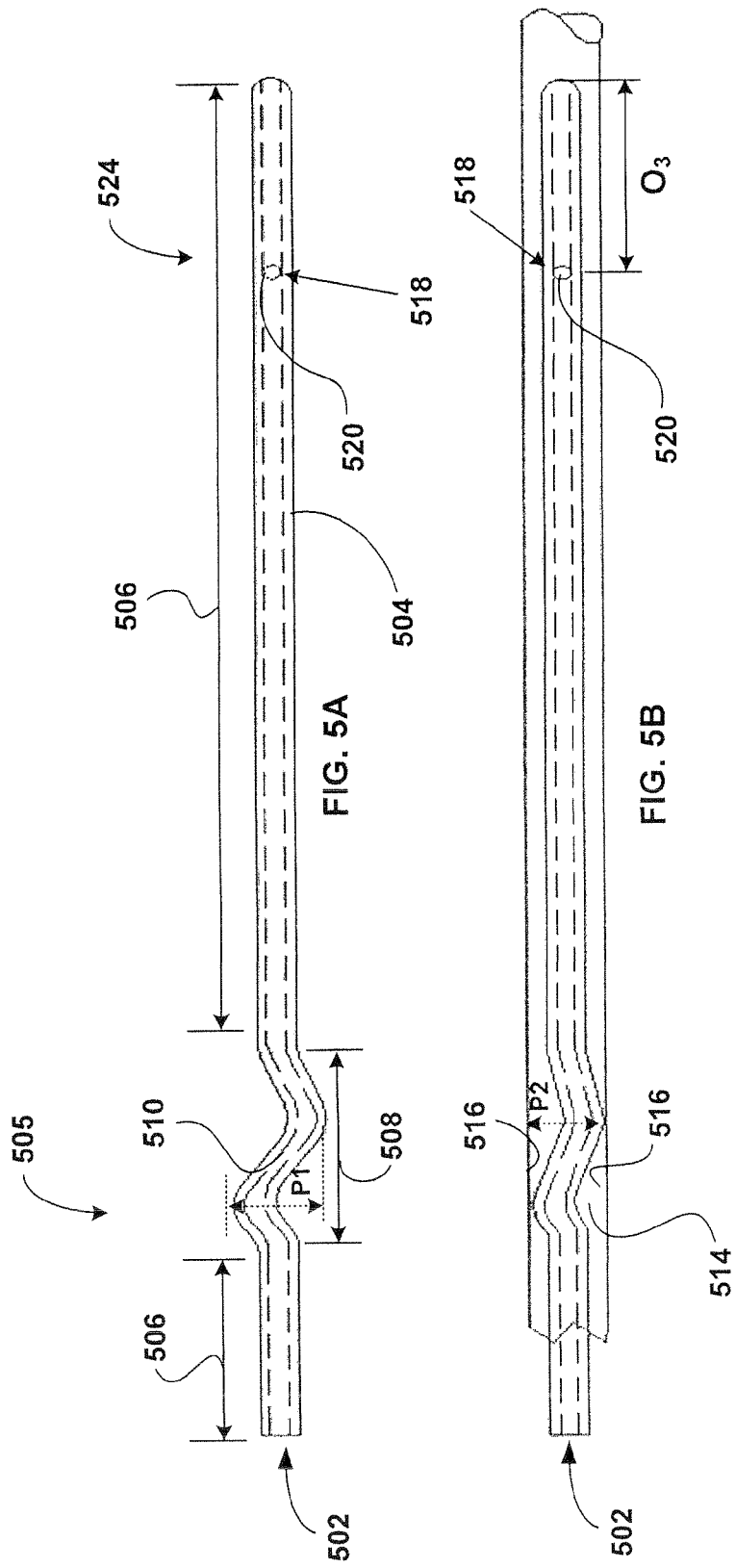

CANNULA IMPLANT DEVICE FOR USE IN SALIVARY GLAND DUCTS

CROSS-REFERENCES TO RELATED APPLICATIONS

This application claims priority to U.S. provisional application Ser. No. 61/362,985, filed Jul. 9, 2010, and to U.S. provisional application Ser. No. 61/423,968, filed Dec. 16, 2010, the entirety of both which is incorporated herein by reference.

FIELD OF THE INVENTION

The instant invention is directed to a medical implant device. More particularly, the instant invention is directed to a medical implant device used in the treatment of salivary duct channels.

BACKGROUND OF THE INVENTION

Salivary glands are found in and around a person's mouth and throat. The major salivary glands are the parotid, submandibular, and sublingual glands. These glands provide the needed saliva to assist in food chewing and early digestion of certain carbohydrates. Saliva is drained through the salivary ducts near the upper teeth, submandibular under the tongue, and the sublingual.

Among the different salivary gland problems encountered, obstruction to the flow of saliva via the salivary gland ducts may be the most common. This may be caused by the formation of stones, which can become lodged in the duct. Thus, as saliva produced in the salivary gland it cannot exit the ductal system and enter the oral cavity. The lack of saliva flow contributes to dry mouth disorder and can cause swelling of the salivary gland, leading to pain and possible infection.

Other problems may include the development of kinks in the salivary gland ducts, stenosis (i.e., constriction or narrowing) of the salivary gland ducts, or generally, other structural or structurally related defects associated with the salivary glands and/or salivary gland ducts.

It is therefore advantageous to facilitate the integrity of the salivary ducts and their respective glands, and to treat glands rather than remove them.

SUMMARY OF THE INVENTION

It is an object of the invention to provide an implant device that is operable, among other functions, to maintain, repair, and/or restore the structure and functionality of salivary gland ducts, and that is simple to remove once this is accomplished.

According to one embodiment, a cannula for placement within a salivary gland duct having a first end adjacent an oral cavity and a second end adjacent a salivary gland is provided. The cannula comprises an elongate body having a lumen, and a first and a second plate offset from the proximal end of the elongate body. The first plate is located on one side of the elongate body and the second plate is located on the other side of the elongate body and adjacent the first plate. The first plate includes a first hole operable to suture the first plate to a location adjacent the first end of the salivary duct adjacent the oral cavity. Upon placement of the cannula within the salivary gland duct, saliva flows through the lumen from the salivary gland to the oral cavity.

According to one embodiment, a stylet device having a substantially rigid structure is provided, whereby the stylet is insertable and removable relative to the lumen of the cannula's elongate body and includes an overall diameter that is less than that of the lumen. The stylet device is inserted into the lumen to provide a backbone structure for facilitating the placement of the cannula within the salivary gland duct.

According to another embodiment, a support tube implant device for placement within a salivary gland duct having a first end adjacent an oral cavity and a second end adjacent a salivary gland is provided. The implant device comprises an elongate body having an outer surface, and a first and a second plate offset from a proximal end of the elongate body. The first plate is located on one side of the elongate body and the second plate is located on the other side of the elongate body and adjacent the first plate. The first plate includes a first hole operable to suture the first plate to a location adjacent the first end of the salivary duct adjacent the oral cavity. Upon placement of the implant device within the salivary gland duct, saliva flows between the outer surface of the elongate body and an inner surface associated with the salivary gland duct.

According to yet another embodiment, a cannula for placement within a salivary gland duct having inner walls is provided. The cannula includes an elongate body and a discontinuity section located at a proximal end portion of the elongate body. Upon placement of the cannula at a position within the salivary gland duct, the discontinuity section is adapted to expand against the inner walls of salivary gland duct for maintaining the position of the cannula within the salivary gland duct. The elongate body of the cannula may also include a lumen that is operable to deliver medication to the salivary gland duct. Moreover, the discontinuity section may include a wave-shape section having a first peak-to-peak height that is adapted to contract to a second peak-to-peak height upon insertion with the salivary gland duct.

According to yet another embodiment, a method is provided for implanting a cannula within a salivary gland duct having a first end adjacent an oral cavity and a second end adjacent a salivary gland. The cannula includes an elongate body having a lumen, and a first and a second plate offset from a proximal end of the elongate body, where the first plate is located one side of the elongate body and the second plate is located the other side of the elongate body and adjacent the first plate. The method of implanting includes inserting a guide wire within the salivary gland duct, whereby the guide wire is inserted to at least an extent that the cannula is intended to be positioned within the salivary duct. The elongate body is placed over the inserted guide wire such that a portion of the guide wire lies within the lumen of the elongate body. The elongate body is then inserted at the intended position within the salivary duct, whereby the first plate is sutured at least to a location within the oral cavity adjacent the first end of the salivary gland duct. The proximal end of the elongate body extends into the oral cavity by an amount corresponding to the offset. The guide wire is then removed from within the lumen of the elongate body when the elongate body is at the intended position within the salivary duct.

According to yet another embodiment, a method is provided for implanting a cannula within a salivary gland duct having inner walls. The cannula includes an elongate body having a lumen and a discontinuity section located at a proximal end portion of the elongate body. The implanting method includes inserting a guide wire within the salivary gland duct, wherein the guide wire is inserted to at least an extent that the cannula is intended to be positioned within the salivary duct. The elongate body is placed over the inserted guide wire such that a portion of the guide wire lies within the lumen of the elongate body. The elongate body is then inserted within the salivary duct. Upon placement of the cannula at the intended position within the salivary gland duct, the discontinuity section is adapted to expand against the inner walls of the salivary gland duct for maintaining the cannula at the intended position within the salivary gland duct. The guide wire is then removed from within the lumen of the elongate body when the elongate body is at the intended position.

According to yet another embodiment, a method of implanting a cannula within a salivary gland duct having a first end adjacent an oral cavity and a second end adjacent a salivary gland is provided. The cannula includes an elongate body having a lumen, and a first and a second plate offset from a proximal end of the elongate body, where the first plate is located on one side of the elongate body and the second plate is located on the other side of the elongate body and adjacent the first plate. The method comprises providing a stylet device for insertion within the lumen of the elongate body, whereby the stylet increases the rigidity of the elongate body. The stylet device is inserted within the lumen of the elongate body, where the stylet extends at least between the proximal end and the distal end of the elongate body. The stylet and elongate body are then inserted within the salivary duct such that the first and the second plate are adjacent the oral cavity and the distal end of the elongate body is adjacent the salivary gland. At least the first plate is sutured to a location within the oral cavity adjacent the first end of the salivary gland duct, whereby the proximal end of the elongate body extends into the oral cavity by an amount corresponding to the offset. The stylet device is then removed from within the lumen of the elongate body when the elongate body is inserted within the salivary duct.

According to another embodiment, a method of implanting a support tube implant device within a salivary gland duct having a first end adjacent an oral cavity and a second end adjacent a salivary gland is provided. The implant device includes an elongate body having an outer surface, and a first and a second plate offset from a proximal end of the elongate body. The first plate is located on one side of the elongate body and the second plate is located on the other side of the elongate body and adjacent the first plate. The method comprises inserting the elongate body within the salivary duct such that the first and the second plate are adjacent the oral cavity and the distal end of the elongate body is adjacent the salivary gland. At least the first plate is then sutured to a location within the oral cavity adjacent the first end of the salivary gland duct, where the proximal end of the elongate body extends into the oral cavity by an amount corresponding to the offset. Saliva flows from the salivary gland to the oral cavity by flowing between the outer surface of the elongate body and an inner surface associated with the salivary duct.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which:

FIG. 3A illustrates the flow of saliva in a support tube implant device and a cannula implant device, respectively;

FIGS. 3B-3C illustrate the flow of medication in a cannula implant device and a support tube implant device, respectively;

FIG. 5A-5B illustrates another exemplary embodiment of a cannula implant device from a side view perspective according to an aspect of the present invention.

DETAILED DESCRIPTION OF THE INVENTION

The instant invention will now be described more fully hereinafter with reference to the accompanying drawings, in which embodiments of the invention are shown. This invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art.

The following embodiments of the present invention describe an implant device that is operable for use in association with the salivary ducts of a patient. Particularly, such an implant device is placed within a salivary duct over a predefined period of time (e.g., two weeks) in order to restore the physical and/or functional integrity of the duct by, for example, facilitating the flow of saliva.

Figure 1A:
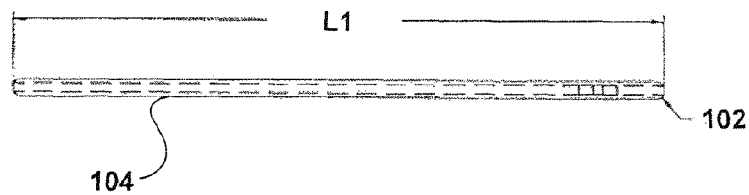
FIG. 1A illustrates an exemplary embodiment of a cannula implant device from a side view perspective according to an aspect of the present invention.

In accordance with one exemplary embodiment, as illustrated in FIG. 1A, a suitable implant device may be comprised of a cannula 102 that includes an elongate body 104 having a length of about 50-90 millimeters (mm). The elongate body 104 of the illustrated cannula 102 typically may have a length L1 of about 79 mm and a substantially uniform circular cross section. Both the inner and outer surfaces of the elongate body 104 may be coated with Paralyene or any other suitable coating material that both facilitates the insertion of the cannula 102 within a duct (not shown) and prevents tissue buildup or growth (i.e., non-biointegratable) during the implantation period, prevents adhesion to the duct walls, allowing for ease of removal, and allows for free flow of saliva inside and outside of the cannula. The cannula's elongate body 104 may be produced from a soft/flexible material such as, but not limited to, silicone rubber, which upon insertion within the salivary duct, provides a requisite degree of comfort for the patient.

Figure 1B:
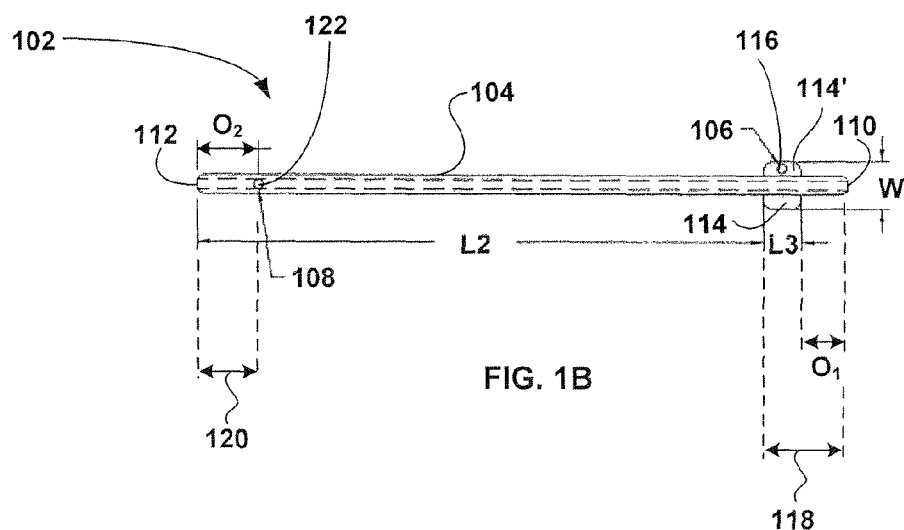
FIG. 1B illustrates the exemplary embodiment of the cannula implant device illustrated in FIG. 1A from a plan view perspective.

FIG. 1B is a plan view of the cannula 102 illustrated in FIG. 1A. As shown, the cannula 102 may be comprised of suturing regions 106 and 108 that are offset from the proximal end 110 and the distal end 112 of the elongate body 104, respectively. Suturing region 106 may include suturing plates 114 and 114' that may each be located on either side of the elongate body 104, and offset from the proximal end 110 by a distance $O_1$. Suturing region 106 also may include a suturing hole 116 for suturing the proximal end portion 118 of the cannula 102 to an area of the oral cavity that may be approximately adjacent to the end of the salivary duct from which saliva flows. Although suturing hole 116 may be located within plate 114', an alternative or additional hole (not shown) may be provided within plate 114. In terms of dimensions, the width W of the suturing plates may be about 5 mm, while the length of the plates L3 may be approximately 4 mm. The length of offset $O_1$ from the proximal end 110 may be about 5 mm. The diameter of suturing hole 116 may be approximately 1 mm.

The suturing hole 116 may be offset from the proximal end 110 of the cannula 102 in order to position the cannula's proximal end 110 away from the end of the salivary duct. Since one of the primary functions of the cannula is to be a conduit for the flow of saliva, the extension of the cannula 102 into the oral cavity caused by suturing region 106 being offset from the proximal end 110 may allow the saliva to flow more effectively into the oral cavity.

Similarly, suturing region 108 may include a suturing hole 122 for optionally suturing the distal end portion 120 of the cannula 102 to a region that may be approximately adjacent to the salivary gland and located at the other end of the salivary duct into which saliva from the gland flows.

Suturing region 108 may be offset from the proximal end 110 by a distance $O_2$. The length of offset $O_2$ from the distal end 112 may be about 10 mm. The diameter of the suturing hole 122 may be approximately 0.5 mm. Suturing region 108 may provide a means for placing the cannula 102 within a salivary gland duct in a retrograde manner. Accordingly, suturing plates 114 and 114' may be removed so that the proximal end 110 of the cannula 102 may be inserted into the salivary duct opening located at the salivary gland. The use of suturing region 108 and its respective suturing hole 122 may provide an alternative means for placement of the cannula 102 when inserting the cannula 102 from the oral cavity end of the salivary duct may be impractical or impossible. This procedure involving the use of suturing region 108 may, however, require some surgical cutting in order to access the salivary duct via the salivary gland.

Figure 1C:
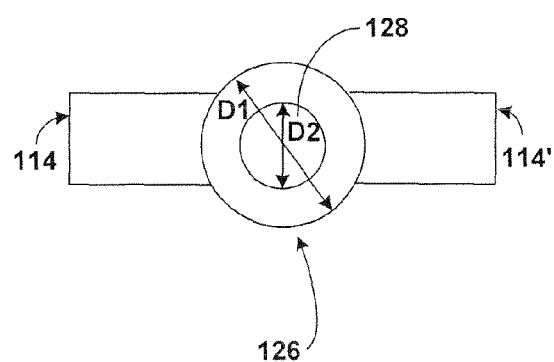
FIG. 1C illustrates the exemplary embodiment of the cannula implant device illustrated in FIG. 1A from an end view perspective.

FIG. 1C depicts an end view of the cannula 102 illustrated in FIGS. 1A and 1B. Accordingly, FIG. 1C illustrates a substantially circular cross-section 126 associated with the elongate body 104 of the cannula 102. Although, the elongate body 104 of the cannula 102 preferably has a circular cross-section, an elliptical or alternatively shaped cross-section may be contemplated based on the physical repair or remedy needed for the particular duct receiving the cannula 102. As shown, elongate body 104 may include a lumen 128 (i.e., the bore of the tube shaped elongate body 104) that may have a diameter D2 of approximately 0.56 mm. The lumen 128 may, however, include any diameter in the range of about 0.40 to 0.75 mm. The overall total diameter D1 of the elongate body 104 may be about 1.5 mm. The elongate body 104 may, however, include any overall total diameter in the range of about 1.0 to 2.0 mm The lumen 128 may provide a conduit for the flow saliva within the cannula 102 when the cannula 102 may be placed or implanted within the salivary duct.

Figure 2A:
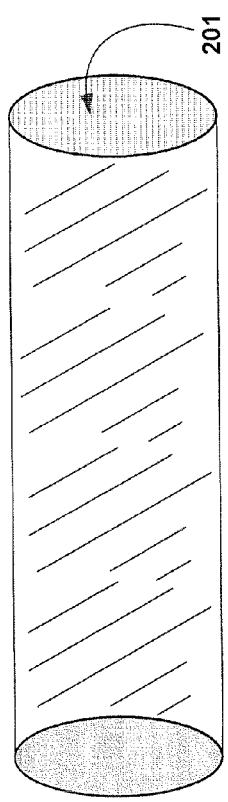
FIG. 2A illustrates an exemplary embodiment of support tube implant device according to an aspect of the present invention.
Figure 2B:
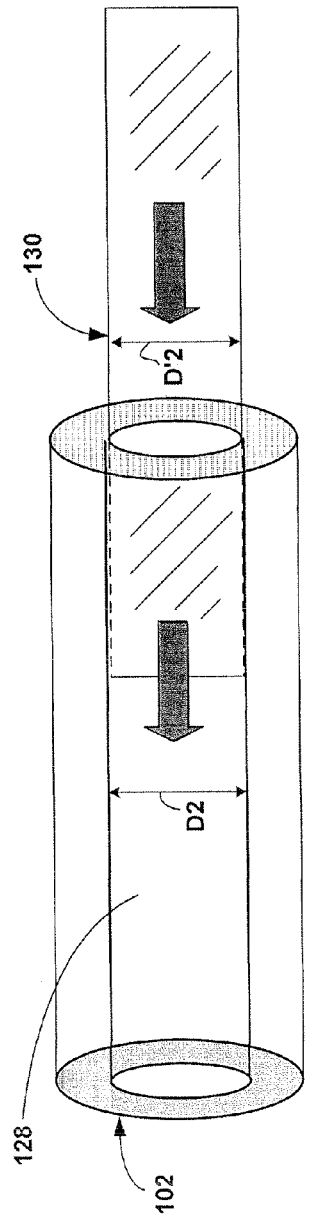
FIGS. 2B-2C illustrate another exemplary embodiment of a support tube implant device according to an aspect of the present invention.
Figure 2C:
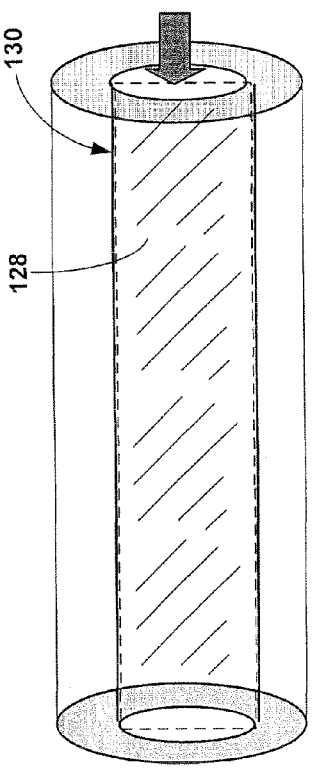

According to some medical circumstances, a cannula may be required to provide more structural support to the salivary duct. If the cannula is constructed from a flexible material such as silicone rubber as described previously, the application of additional rigidity or a back-bone structure to the cannula may be needed. Thus, as illustrated in FIG. 2A, a support tube implant device 201 with an increased rigidity may be created by removing the lumen 128 (FIG. 1C) within the elongate body 104 of cannula 102. Accordingly, the hollow interior space formed by the lumen 128 may be filled by, for example, silicone rubber, such that elongate body 104 becomes a solid tube having no interior space (see FIG. 2A). Alternatively, as illustrated in FIGS. 2B and 2C, the existing lumen 128 of cannula 102 (FIG. 1C) may be filled with a rod 130 that has a diameter D'2 that may be substantially the same as the diameter D2 of the lumen 128, and a length that may be substantially the same or less than that of the cannula 102. Thus, the cannula 102 may be converted to a support tube implant device such as the support tube implant device 201 described and illustrated in relation to FIG. 2A.

By placing the support tube implant device 201 within a salivary duct, more structural support may be provided to the duct. For example, if damage to the salivary duct is such that a cannula may not be able to restore the shape of the duct, a more rigid support tube implant device such as device 201 may be used. However, since the flow of saliva is important, as illustrated in FIG. 3A, the overall diameter of the implant device 201 may be selected so that saliva 300 flows (as depicted by the arrows) between the outer surface 302 of the support tube implant device 201 and the inner surface 304 of the salivary duct 301 (FIG. 3A).

The lumen 128 of cannula 102 may also facilitate the direct delivery of drugs to the posterior region of the salivary gland (not shown). As illustrated in FIG. 3B, medication 350, suspended in a solution, can be introduced into the anterior end (Arrow A) of the cannula 102 with the aid of a syringe (Not shown). The suspension may travel through the lumen 128 of the cannula 102 and exit at the distal end (Arrow B). Referring to FIG. 3C, there may be cases where it may be beneficial for the medication 350 to travel between the cannula's outer-surface 310 and the salivary duct walls 312. This may be possible as a result of the outer coating (e.g., PTFE) of the outer-surface 310 of the cannula 102. The coating may prevent the adhesion of the cannula's 102 outer-surface 310 to the salivary duct walls 312, which may allow for the medication 350 to flow anteriorly. The control of the flow, or prevention of flow/migration if necessary, may be defined by the viscosity of the medication. A viscous fluid, for example, may stay in the posterior area of the duct, and a less viscous fluid may flow over the cannula throughout the salivary duct.

Figure 4A:
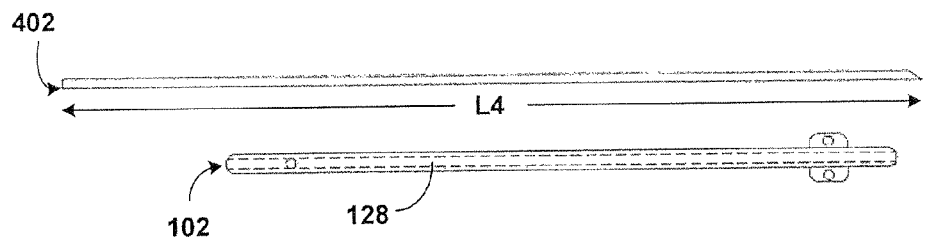
FIG. 4A illustrates a stylet device corresponding to a cannula implant device according to an aspect of the present invention.
Figure 4B:
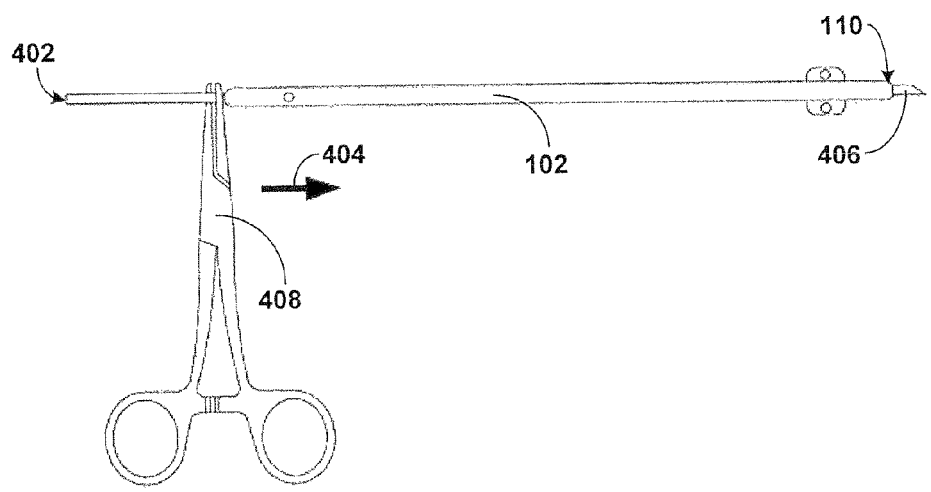
FIGS. 4B-4C illustrate the use of the stylet device of FIG. 4A in association with the corresponding cannula implant device.

As illustrated in the exemplary embodiment of FIG. 4A, a solid substantially rigid stylet (or insertion member) 402 may be used in order to facilitate the insertion of the cannula 102 within a salivary duct. By placing the stylet 402 within the lumen 128, the requisite rigidity for this insertion procedure may be provided to the cannula 102. FIG. 4B shows the stylet 402 fully inserted within the cannula's 102 lumen 128 (FIG. 4A) in the direction of arrow 404, whereby the end 406 of the stylet 402 extends beyond the proximal end 110 of the cannula 102. As illustrated in FIG. 4B, forceps 408 may be used as a braking mechanism to inhibit the cannula 102 and stylet 402 from moving with respect to one another once the stylet 402 is inserted either entirely or to a desired portion within the cannula's 102 lumen 128. In order to facilitate the easy insertion and removal of the stylet 402 with respect to the lumen 128 of the cannula 102, the stylet may include an overall diameter that is slightly less than the overall diameter of the lumen 128. In addition, the ease of insertion and removal of the stylet 402 may be further complemented by the stylet's 402 Paralyene or Polytetrafluoroethylene (PTFE) outer coating, which may reduce friction between the outer surface of the stylet 402 and the inner surface of the lumen 128. The length (L4) of the stylet (FIG. 4A) is in the range of about 120-150 mm.

Figure 4C:
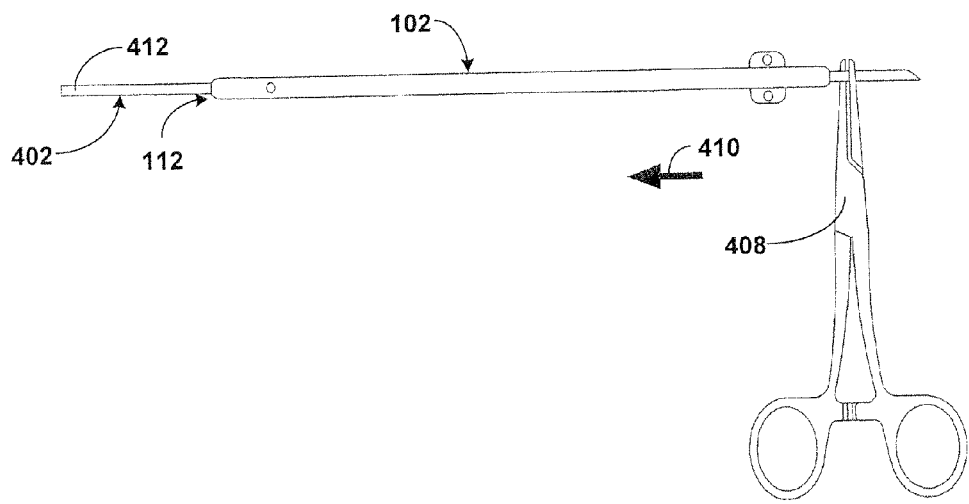

FIG. 4C shows the stylet 402 fully inserted within the cannula's 102 lumen 128 (FIG. 4A) from the opposite direction, as depicted by arrow 410, whereby the other end 412 of the stylet 402 extends beyond the distal end 112 of the cannula 102. As illustrated, forceps 408 may be once again used as a braking mechanism to inhibit the cannula 102 and stylet 402 from moving with respect to one another once the stylet 402 is inserted either entirely or to a desired portion within the cannula's 102 lumen 128.

Figure 4D:
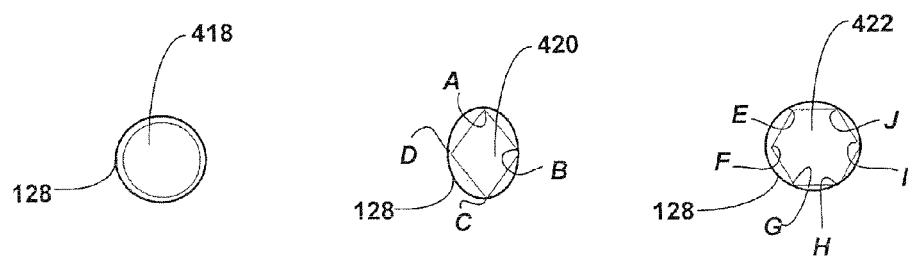
FIG. 4D illustrates various cross section profiles for a stylet device according to different embodiments of the present invention.
Figure 4E:
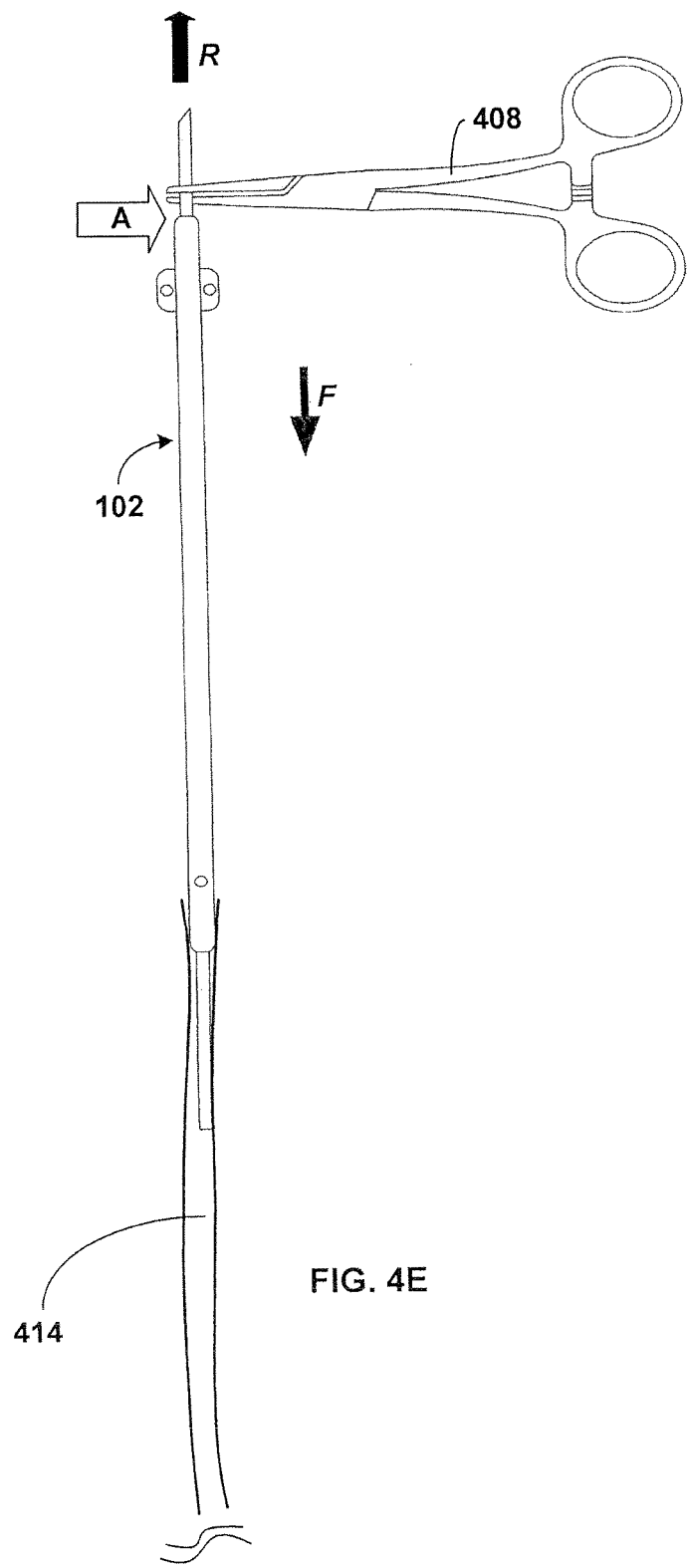
FIG. 4E illustrates the insertion of a cannula device within a salivary duct using a stylet device according to an embodiment of the present invention.

In this manner, as illustrated in FIG. 4E, since the forceps 408 are providing a braking mechanism at point A (FIG. 4B), the forceps 408 may apply a simultaneous force (arrow F) to both the stylet 402 and cannula 102 in order to move the cannula 102 along the salivary duct 414. Meanwhile, during this process, the stylet 402 may provide the rigidity needed for moving the cannula 102 and stylet 402 along the duct 414. Once the cannula 102 is placed within the duct 414, the stylet 402 may be removed using the forceps 408 by pulling the stylet 402 in direction R.

FIG. 4D illustrates several cross-sections for a stylet according to different embodiments. For example, stylet 402 (FIG. 4A) may have a substantially circular or oval cross section such as cross section 418. With cross section 418, a stylet such as stylet 402 may have an increased frictional relationship when introduced within the lumen 128 (FIG. 4A) of cannula 102. This increased frictional relationship may arise as a result of most of the outer surface of the stylet 402 coming into contact with the inner surface of the lumen 128. According to another example, stylet 402 (FIG. 4A) may have a substantially rectangular cross section such as cross section 420. With cross section 420, a stylet such as stylet 402 may have a reduced frictional relationship when introduced within the lumen 128 (FIG. 4A) of cannula 102. This reduced frictional relationship may arise as a result of a reduced outer surface of the stylet 402 coming into contact with the inner surface of the lumen 128. Particularly, such a stylet will make contact with the inner surface of the lumen 128 at points A, B, C, and D. According to yet another example, stylet 402 (FIG. 4A) may have a substantially multi-sided cross section (e.g., hexagonal shape) such as cross section 422. With cross section 422, a stylet such as stylet 402 may have a slightly reduced frictional relationship when introduced within the lumen 128 (FIG. 4A) of cannula 102. This slightly reduced frictional relationship may arise from the reduced outer surface of the stylet 402 coming into contact with the inner surface of the lumen 128. Particularly, such a stylet will make contact with the inner surface of the lumen 128 at points E, F, G, H, I, and J. Cross section 422 may have an increased frictional relationship compared to cross section 420 when introduced within the lumen 128 (FIG. 4A) of cannula 102. This may occur as a result of cross section 422 having more points of contact (i.e., six points of contact: E-J) with the inner surface of the lumen 128 than cross section 420, which as illustrated has less points of contact (i.e., four points of contact: A-D). Therefore, by shaping the cross section of the stylet, it may be possible to control the frictional relationship the stylet has with the inner surface of a cannula lumen. Thus, the requisite force associated with inserting and removing the stylet become controllable based on a cross section factor, whereby the cross section factor may include, for example, the shape of the cross section and/or the number of sides (n) of a multisided cross section (n=3 or more).

Figure 4F:
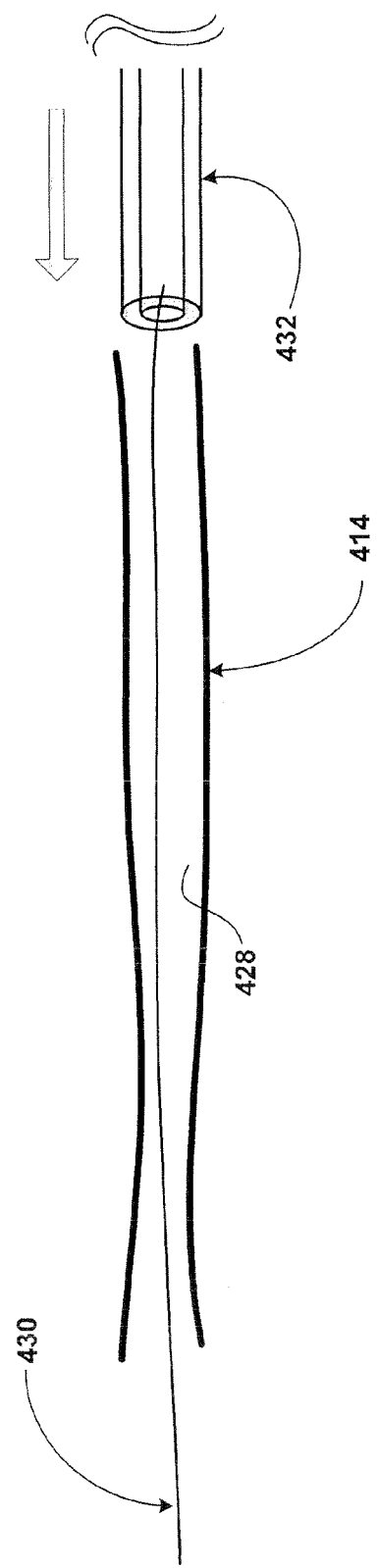
FIG. 4F illustrates the insertion of a cannula device within a salivary duct using a guide wire according to an embodiment of the present invention.

Also, a guide wire may be additionally utilized. As illustrated in FIG. 4F, a guide wire 430 may be flexible and may provide a physician with the advantage of placing the guide wire 430 through the extent 428 of a convoluted salivary duct 414 prior to the introduction of a cannula device. Once the physician is comfortable with the position of the guide wire within the duct, he can introduce the cannula 432 over the guide wire thereby insuring an appropriate positioning of the cannula.

For example, in use, the cannula and/or support tube implant device may be used in association with the sublingual gland. Also, the suturing may be carried out using known methods. For example, the suturing hole 116 (FIG. 1B) within suturing the plate 114' may be used to suture the cannula and/or support tube implant device to either the mucosa or periosteum near the lingual side of the anterior teeth within the oral cavity.

In accordance with another exemplary embodiment, as illustrated in FIG. 5A, another suitable implant device may be comprised of a cannula 502 that includes an elongate body 504 having a substantially uniform circular cross section along elongate sections 506. The remaining section 508 at the proximal end portion 505 of the cannula 502 may include a discontinuity or convoluted shape 510 that facilitates the anchoring of the cannula 502 when placed within a salivary duct 514 (see FIG. 5B). As previously described, the outer surface of the elongate body 504 may be coated with Paralyene or any other suitable coating material that both facilitates the insertion of the cannula 502 within the salivary duct 514 and prevents tissue build-up or growth (i.e., non-biointegratable) during the implantation period. As shown in FIG. 5B, the discontinuity or convoluted shape 510 may take the form of a wave-shape (e.g., triangular or saw-tooth wave shape) capable of being contracted when inserted into the salivary duct 514. The contracted wave-shape discontinuity 510 then may exert pressure against the walls of the salivary duct 514, which in turn may retain the position of the cannula 502 within the salivary duct 514 and in some instances eliminates any necessity for suturing the cannula 502. The discontinuity or convoluted shape 510 may take the form of any contractible region that accordingly expands from its contracted state once placed within the salivary duct 514. The expansion of the contractible region then may exert a requisite pressure against the stiff walls 516 of the salivary duct 514 for maintaining the position of the cannula 502 within the salivary duct 514. The resistance required to dislodge the cannula 502 from the salivary duct 514 may be substantial enough to ensure that the cannula 502 will not extrude from its position once appropriately placed in the duct. For example, prior to inserting the cannula 502, the wave-shape discontinuity 510 has a peak-to-peak height of P1. Following the insertion or placement of the cannula 502 within the duct 514, the peak-to-peak height of the wave-shape discontinuity 510 may contract to P2 as a result of the physical dimensions of the duct 514 being smaller than that of the peak-to-peak height (P1) of the wave-shape discontinuity 510 prior to insertion within the duct 514. Cannula 502 also may include a suturing region 518 having a suturing hole 520 for optionally suturing the distal end portion 524 of the cannula 102 to a region that is approximately adjacent to the salivary gland and located at the other end of the salivary duct into which saliva from the gland flows. Suturing region 518 may be offset from the proximal end 110 by a distance $O_3$.

Although a preferred embodiment of the present invention and modifications thereof have been described in detail herein, it is to be understood that this invention is not limited to this precise embodiment and modifications, and that other modifications and variations may be effected by one skilled in the art without departing from the spirit and scope of the invention as defined by the appended claims.

What is claimed is:

1. A method of implanting a cannula within a salivary gland duct having a first end adjacent an oral cavity and a second end adjacent a salivary gland, the cannula comprising an elongate body having a lumen, and a first and a second plate offset from a proximal end of the elongate body, the first plate located one side of the elongate body and the second plate located the other side of the elongate body and adjacent the first plate, the method comprising:

inserting a guide wire within the salivary gland duct, wherein the guide wire is inserted to at least an extent that the cannula is intended to be positioned within the salivary gland duct;

placing the elongate body over the inserted guide wire such that a portion of the guide wire lies within the lumen of the elongate body;

inserting the elongate body at the intended position within the salivary gland duct;

suturing at least the first plate to a location within the oral cavity adjacent the first end of the salivary gland duct, wherein the proximal end of the elongate body extends into the oral cavity by an amount corresponding to the offset; and removing the guide wire from within the lumen of the elongate body when the elongate body is at the intended position within the salivary gland duct.

* * * * *